(12) United States Patent
Fontana

(10) Patent No.: US 7,712,991 B2
(45) Date of Patent: May 11, 2010

(54) APPLICATOR FOR FLUID SUBSTANCES FOR MEDICAL AND/OR COSMETIC USE

(75) Inventor: Antonio Fontana, Carpi (IT)

(73) Assignee: Lameplast S.p.A., Rovereto sul Secchia (MO) (IT)

( * ) Notice: Subject to any disclaimer, the term of this patent is extended or adjusted under 35 U.S.C. 154(b) by 338 days.

(21) Appl. No.: 11/571,793

(22) PCT Filed: Jul. 13, 2005

(86) PCT No.: PCT/EP2005/053339

§ 371 (c)(1),
(2), (4) Date: Jan. 8, 2007

(87) PCT Pub. No.: WO2006/008255

PCT Pub. Date: Jan. 26, 2006

(65) Prior Publication Data
US 2008/0304898 A1 Dec. 11, 2008

(30) Foreign Application Priority Data
Jul. 16, 2004 (IT) .......................... MO2004A0184

(51) Int. Cl.
*B43K 5/14* (2006.01)
(52) U.S. Cl. ..................... 401/134; 401/133; 401/202
(58) Field of Classification Search ......... 401/132–135, 401/202, 205, 207
See application file for complete search history.

(56) References Cited

U.S. PATENT DOCUMENTS

| | | | |
|---|---|---|---|
| 4,599,008 A | 7/1986 | Furlong et al. | |
| 5,042,690 A * | 8/1991 | O'Meara | ..................... 222/83 |
| 5,131,777 A * | 7/1992 | Kimura et al. | .............. 401/202 |
| 5,193,928 A | 3/1993 | Balzer et al. | |
| 6,505,985 B1 * | 1/2003 | Hidle et al. | .................. 401/134 |
| 7,431,529 B1 * | 10/2008 | Rushe et al. | ................ 401/269 |
| 2002/0057939 A1 | 5/2002 | Gueret | |

* cited by examiner

*Primary Examiner*—David J Walczak
(74) *Attorney, Agent, or Firm*—Dykema Gossett PLLC

(57) ABSTRACT

An applicator (1) for fluid substances for medical and/or cosmetic use comprises a container (2), which is divided by a transverse breakable partition (3) into a first chamber (4) for containing a fluid substance and a second chamber (5), which is spaced in an axial direction from the first chamber (4) and is provided with an opening (6), a piercing element (7), which is associated with the opening substantially hermetically with respect to the substance and so that it can slide axially between a first configuration, in which it does not interfere with the partition (3), and a second configuration, in which it interferes with the partition (3) in order to break it, an axial hole (8) formed through the piercing element (7), a porous pad (9), which is associated with the end of the piercing element (7) that is directed toward the outside of the container (2), and a cap (10) for covering the pad (9), which is detachably associated with the piercing element (7).

10 Claims, 4 Drawing Sheets

APPLICATOR FOR FLUID SUBSTANCES FOR MEDICAL AND/OR COSMETIC USE

TECHNICAL FIELD

The present invention relates to an applicator for fluid substances for medical and/or cosmetic use.

BACKGROUND ART

Applicators for medical and/or cosmetic substances are known which are substantially constituted by a container divided by a transverse breakable membrane into two chambers, which are mutually spaced in an axial direction: a first chamber for containing the substance to be applied and a second chamber provided with an opening with which a sponge-like pad is associated.

A plurality of radial slots of reduced thickness are formed in the membrane and break under the action of a radial compression applied from the outside to the walls of the container at the height of the membrane, forming a corresponding plurality of triangular sectors.

Under the action of the external pressure, the triangular sectors tend to move mutually apart, clearing, at the center of the area occupied by the membrane, an opening for the passage of the substance from the first chamber to the second chamber; the substance can thus be applied.

The size of the opening that is formed varies depending on the amount of pressure applied to the container.

A protrusion is formed on the outer lateral surface of the container, at the height of the membrane, and indicates the point where pressure is to be applied.

However, these known containers are susceptible of further improvements aimed in particular at improving the hygiene of the sponge-like pad both before the first application and between successive applications of the substance contained therein.

Within this aim, an object of the present invention is to provide a structure which is simple, relatively easy to provide in practice, safe in use, effective in operation, and has a relatively low cost.

SUMMARY OF THE INVENTION

This aim and this and other objects that will become better apparent hereinafter are achieved by the present applicator for fluid substances for medical and/or cosmetic use, characterized in that it includes a container, which is divided by a transverse breakable partition into a first chamber for containing a fluid substance and a second chamber, which is spaced in an axial direction from the first chamber and is provided with an opening, a piercing element, which is associated with the opening substantially hermetically with respect to said substance and so that it can slide axially between a first configuration, in which it does not interfere with the partition, and a second configuration, in which it interferes with the partition in order to break it, an axial hole formed through the piercing element, a porous pad, which is associated with the end of the piercing element that is directed toward the outside of the container, and a cap for covering the pad, which is detachably associated with said piercing element.

Further characteristics and advantages of the present invention will become better apparent from the following detailed description of a preferred but not exclusive embodiment of an applicator for fluid substances for medical and/or cosmetic use, illustrated by way of non-limiting example in the accompanying drawings.

DETAILED DESCRIPTION OF THE PREFERRED EMBODIMENTS

Figure 1:
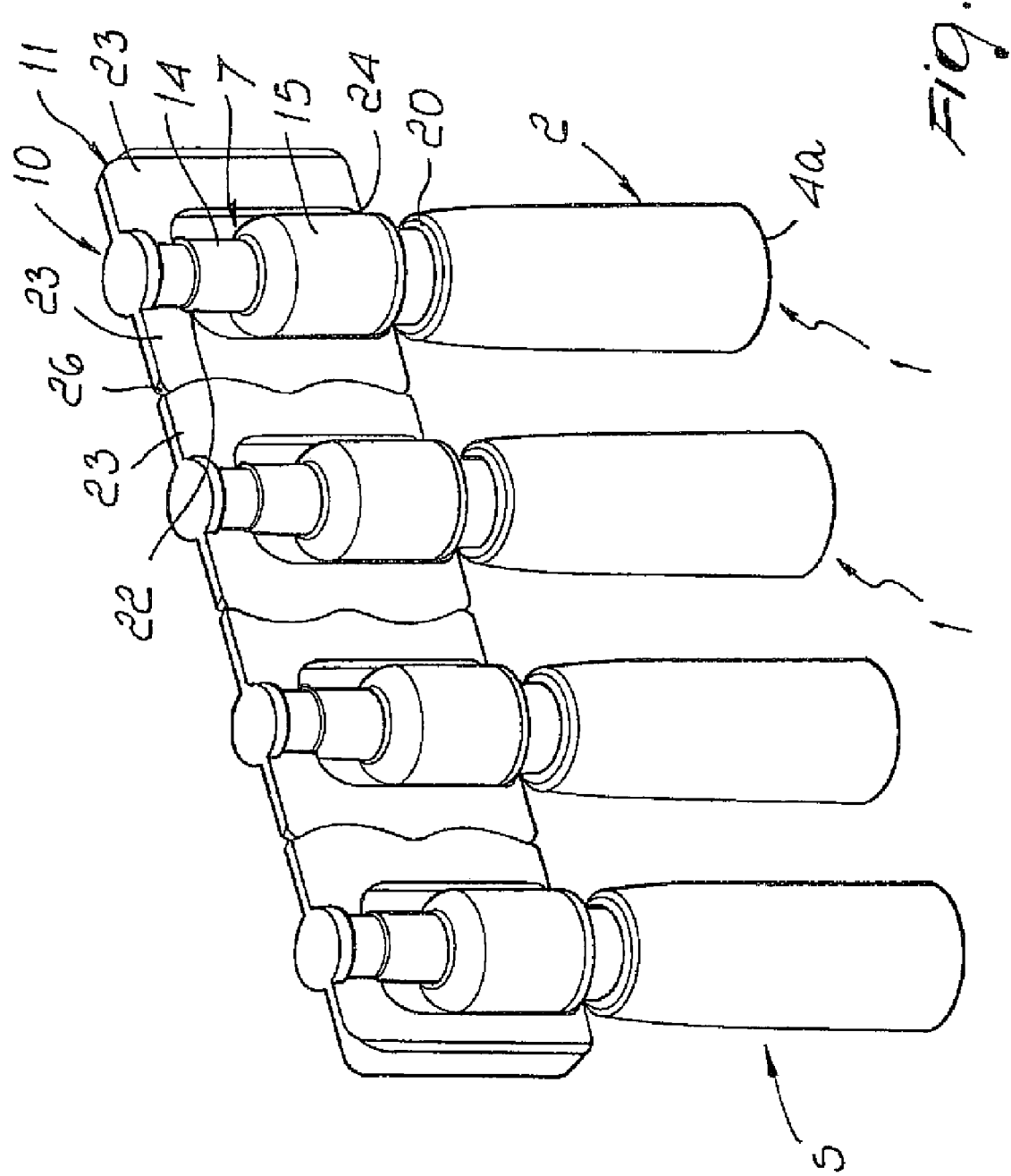
FIG. 1 is a schematic perspective view of a plurality of applicators according to the invention before they are filled.
Figure 2:
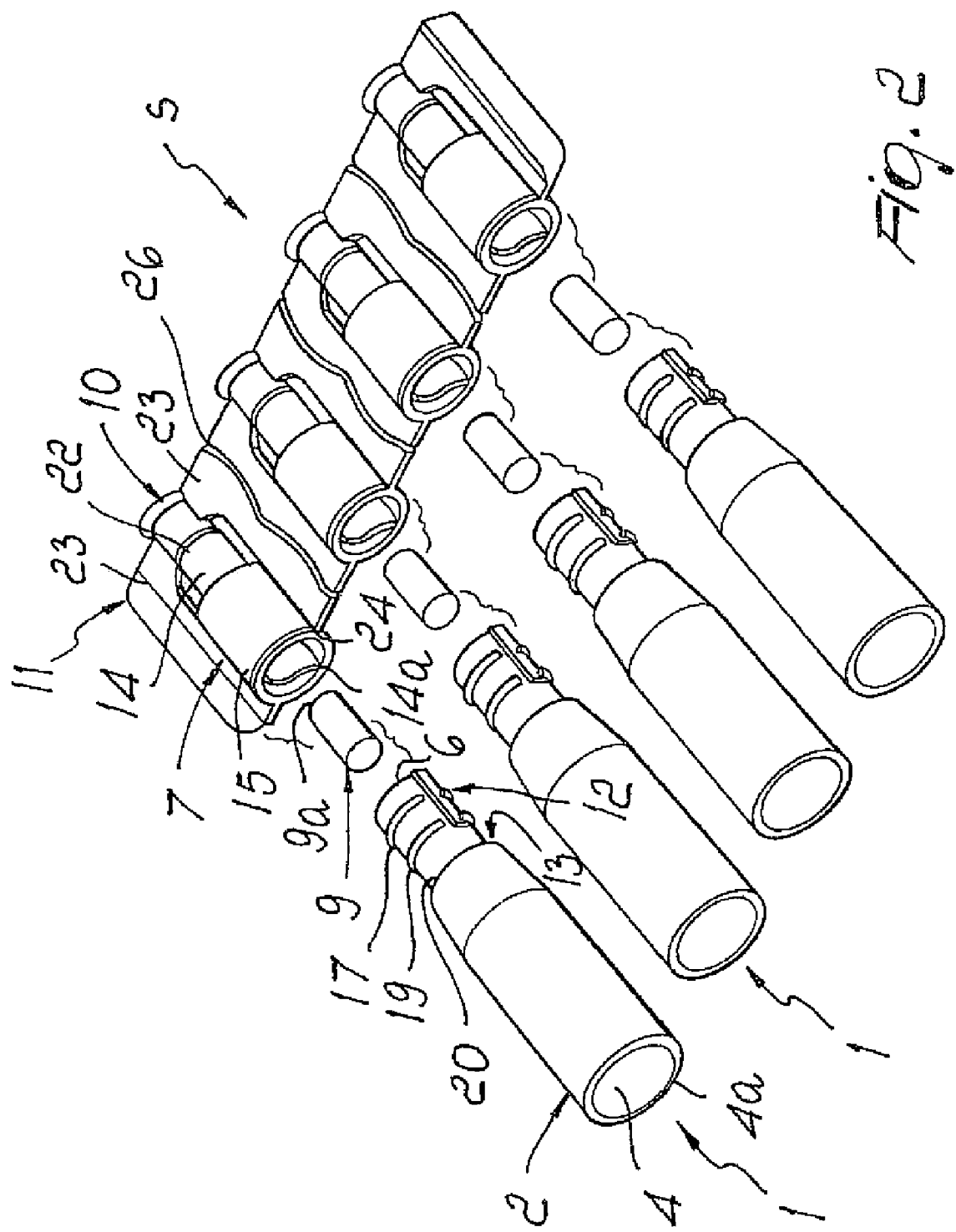
FIG. 2 is a schematic exploded view of the plurality of applicators of FIG. 1.
Figure 3:
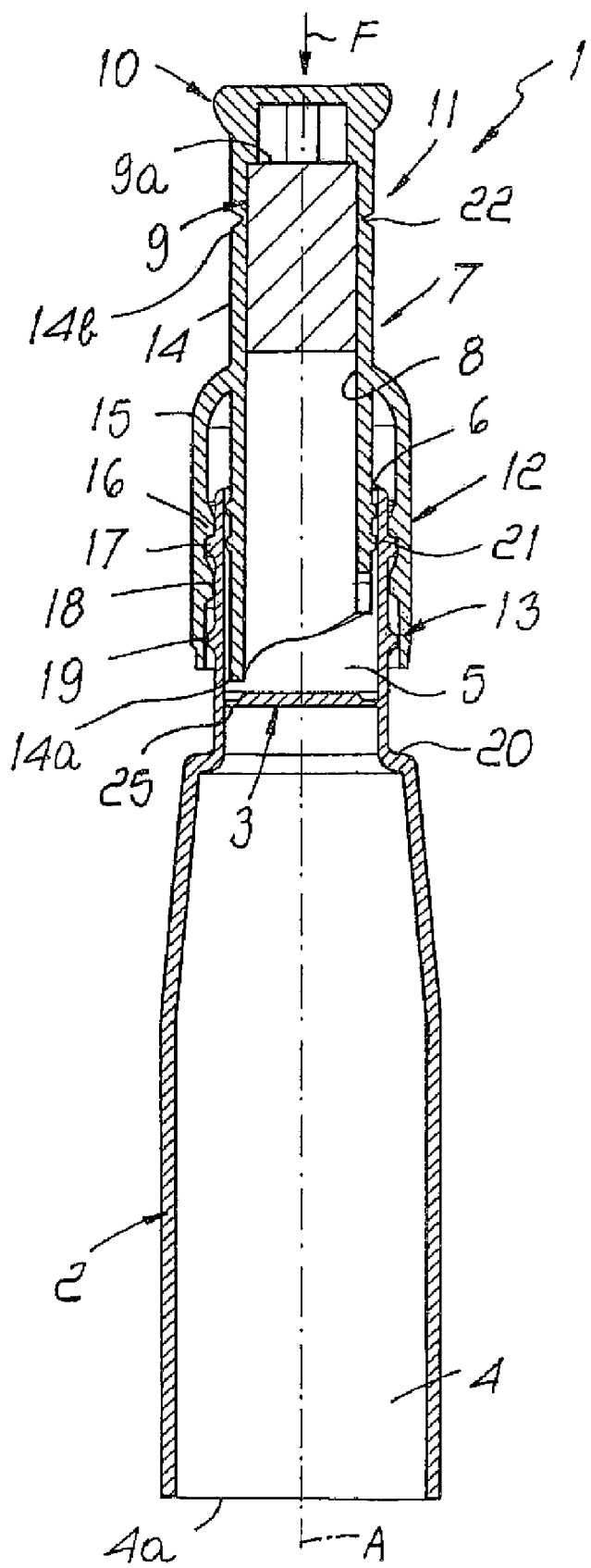
FIG. 3 is a schematic sectional view of an applicator according to the invention in the packaging configuration.
Figure 4:
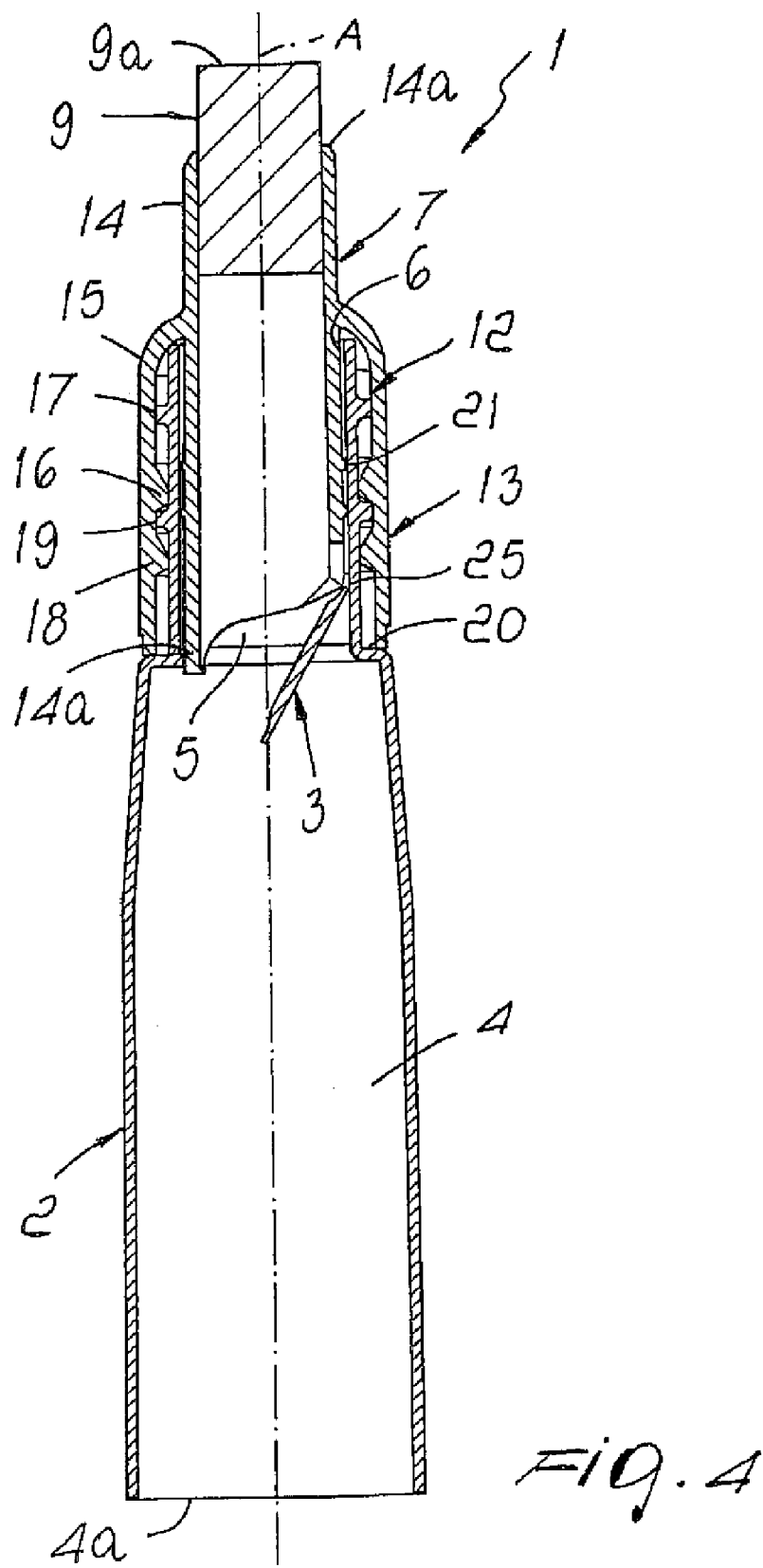
FIG. 4 is a schematic sectional view of an applicator according to the invention in the configuration for use.

With reference to the figures, the reference numeral 1 generally designates an applicator for fluid substances for medical and/or cosmetic use, particularly for substances for dental applications, such as for example anesthetics, disinfectants and the like.

The applicator 1 includes a container 2, which has a longitudinal axis A and is divided by a partition 3, which lies transversely to the axis A and is breakable into a first chamber 4 for containing a fluid substance to be applied, and into a second chamber 5 which is spaced in an axial direction from the first chamber and is provided with an opening 6.

A piercing element 7 is associated with the opening 6, substantially hermetically with respect to the substance contained in the first chamber 4, and can slide axially between a first configuration in which it does not interfere with the partition 3, and a second configuration in which it interferes with the partition 3 in order to break it.

The piercing element 7 is crossed by an axial through hole 8, and its end directed toward the outside of the container 2 is associated with a porous or sponge-like pad 9.

The pad 9 is partially inserted in the hole 8 and is thus connected to the second chamber 5 and partially protrudes from it; the surface 9a of its protruding portion is the surface that allows to distribute the substance on a chosen application surface.

The pad 9 is covered by a cap 10, which is detachably associated with the piercing element 7 by way of tamper-resistant sealing means 11.

Means 12 for temporarily retaining the piercing element 7 in the first configuration and means 13 for stopping the sliding of the piercing element 7 in the second configuration are also provided.

The piercing element 7 is constituted by a central tubular element 14, which forms the hole 8 and in which the opposite ends 14a and 14b are open: one end 14a is inserted in the second chamber 5 and has a sharp contoured profile for breaking the partition 3 and the other end 14b is associated with the pad 9.

The tubular element 14 is partially surrounded by an external sleeve 15, which surrounds the outer lateral surface of the container 2.

The retention means 12 and the stop means 13 are formed between the outer sleeve 15 and the outer lateral surface of the container 2 and respectively comprise two teeth 16-17 and 18-19, which protrude respectively on the internal lateral surface of the sleeve 15 and on the external lateral surface of the container 2 and can be coupled by snap action.

Further, the stop means 13 comprise a surface 20 for the abutment of the lower end of the sleeve 15, which is formed externally to the container 2 and is advantageously constituted by the ring formed by a variation in the cross-section of said container.

Annular expansions 21 for providing a seal with the internal walls of the opening 6 are provided on the outer surface of the tubular element 14.

The tamper-resistant sealing means 11 comprise a tearable portion 22, which is formed between the base of the cap 10 and the perimetric edge of the piercing element 7, and two mutually diametrically opposite wings 23, each of which protrudes from the cap 10 and is associated, along a respective breakable line (bridge portion) 24, with the sleeve 15 of the piercing element 7.

The partition 3 is associated with the internal walls of the container 2 along a weakened perimetric line 25.

The piercing element 7 is obtained monolithically with the cap 10 and with wings 23.

The end 4a of the first chamber 4 that lies opposite the partition 3 is open for the insertion of the substance in the first chamber 4 and is suitable to be closed by heat-sealing or the like after filling.

Conveniently, the applicator 1 can be produced in a series S with other applicators 1, the contiguous wings 23 of two adjacent applicators 1 being mutually joined temporarily along respective breakable lines 26.

The applicator 1 is assembled by inserting the pad 9 in the piercing element 7 through the end 14a of its tubular element 14 and by inserting the piercing element 7 in the opening 6 of the container 2 until the tooth 16 abuts against the corresponding tooth 17.

After inserting the substance to be applied inside the first chamber 4, its open end 4a is closed for example by heat-sealing.

At the time of use, after separating from the series S an end applicator 1 by breaking the breakable line 26 that connects its internal wing 23 to the wing 23 of the applicator 1 that is adjacent thereto, it is necessary to apply to the cap 10, and therefore to the piercing element 7 temporarily coupled thereto by the tamper-resistant sealing means 11, a thrust, designated by the arrow F, in an axial direction in order to cause the piercing element 7 to slide from the first configuration to the second configuration, until the tooth 16 disengages from the corresponding tooth 17, the tooth 18 moves beyond the corresponding tooth 19 with a snap action, and the lower end of the jacket 15 rests against the abutment surface 20.

The cutting profile of the end 14a of the tubular element 14 tears the weakened line 25 that rigidly couples the partition 3 to the internal walls of the container 2, disengaging it from said walls and thus opening a passage between the first chamber 4 and the second chamber 5.

After teasing the tamper-resistant sealing means 11, the cap 10 is removed, exposing the pad 9 to the external environment.

By overturning the container 2 so that the pad 9 faces downward and/or by pressing its side walls, the substance contained in the first chamber 4 passes, through the opening provided by the broken partition 3, into the second chamber 5, where it impregnates, through the hole 8, the pad 9, which releases it through the surface 9a, onto the application surface.

If the substance contained in the first chamber 4 is not used up in a single application, it is possible to replace the cap 10 on the pad 9 in order to cover it and protect it from external agents until the subsequent application.

It is noted that until the first application, the pad 9 is protected with respect to the outside environment by the cap 10, which is conveniently coupled to the piercing element 7.

It is also possible to package in the second chamber 5 a product which can be mixed with the substance contained in the first chamber 4; in this case, the second chamber 5 acts as a tank and the breakage of the partition 3 causes first of all the transfer of the product contained therein into the first chamber 4, where it mixes with the substance contained therein.

In practice it has been found that the described invention achieves the intended aim and object.

The invention thus conceived is susceptible of numerous modifications and variations, all of which are within the scope of the appended claims.

All the details may feather be replaced with other technically equivalent ones.

In practice, the materials used, as well as the shapes and the dimensions, may be any according to requirements without thereby abandoning the scope of the protection of the appended claims.

The disclosures in Italian Patent Application No. MO2004A000184 from which this application claims priority are incorporated herein by reference.

The invention claimed is:

1. An applicator for fluid substances comprising:
   an elongated container which defines an internal lateral surface and an outer lateral surface, a transverse breakable partition within said container which divides said container into a first chamber for containing a fluid substance and a second chamber which is axially spaced from the first chamber and is provided with an opening having internal walls,
   an elongated piercing element which is associated with said opening substantially hermetically with respect to said substance and so that said piercing element can slide axially between a first configuration in which the piercing element does not interfere with said partition, and a second configuration in which the piercing element interferes with said partition in order to break the partition;
   said piercing element defining an axial passageway therethrough;
   a porous pad which is associated with an end of said piercing element remote from said container;
   a cap which covers said pad and is one piece with said piercing element and detachable from said piercing element, an annular portion of reduced thickness separating said cap and said piercing element to provide a tearable, tamper-resistant sealing means between said cap and said piercing element, and
   a wing which extends laterally from said cap for connection to a wing of an adjacent applicator, and includes an end which is connected to said piercing element along a breakable bridge portion.

2. The applicator according to claim 1, further comprising retention means for temporarily retaining said piercing element in said first configuration.

3. The applicator according to claim 2, further comprising stop means for stopping the sliding of said piercing element in said second configuration.

4. The applicator according to claim 3, wherein said piercing element comprises a central tubular element which has outer walls and forms said axial passageway and whose opposite ends are opened, one of said ends being inserted in said second chamber and having a sharp contoured profile for breaking said partition, the other end being associated with said pad, which protrudes partially from said other end, and an external sleeve which has an internal lateral surface which partially surrounds said tubular element and is suitable to wrap around the outer lateral surface of said container, said retention means and said stop means being formed between said sleeve and said outer lateral surface of the container.

5. The applicator according to claim 4, wherein said partition is associated with the internal walls of said container along a weakened line.

6. The applicator according to claim 4, wherein said second chamber is suitable to contain a product which can be mixed with said substance.

7. The applicator according to claim 4, wherein an end of said first chamber remote from said partition is open for the insertion of said substance and is suitable to be closed by heat-sealing.

8. The applicator according to claim 4, wherein said piercing element comprises at least one annular expansion, which is formed on its outer walls of said tubular element for providing a seal with the internal walls of said opening.

9. The applicator according to claim 4, when at least one of said retention means and said stop means comprises at least one pair of teeth formed so as to protrude respectively on the internal lateral surface of said sleeve and on the outer lateral surface of said container.

10. The applicator according to claim 3, wherein said stop means comprises a surface for the abutment of said piercing element, said surface being formed in said container.

* * * * *